United States Patent [19]

Kulpe et al.

[11] Patent Number: 5,591,893
[45] Date of Patent: Jan. 7, 1997

[54] PROCESS FOR THE PREPARATION OF POLYCARBOXYLIC ACIDS AND DERIVATIVES THEREOF

[75] Inventors: Jürgen Kulpe; Heinz Strutz, both of Frankfurt am Main, Germany

[73] Assignee: Hoechst AG, Frankfurt am Main, Germany

[21] Appl. No.: 146,429

[22] Filed: Oct. 27, 1993

Related U.S. Application Data

[63] Continuation of Ser. No. 875,386, Apr. 29, 1992, abandoned.

[30] Foreign Application Priority Data

May 2, 1991 [DE] Germany ............... 41 14 376.0

[51] Int. Cl.⁶ .................................................. C07C 61/06
[52] U.S. Cl. .................. 562/504; 562/509; 562/543; 562/544
[58] Field of Search ..................... 562/543, 544, 562/509, 504

[56] References Cited

U.S. PATENT DOCUMENTS

| | | | |
|---|---|---|---|
| 3,218,353 | 11/1965 | Volkenburgh et al. | 260/514 |
| 3,238,250 | 3/1966 | Bailey | 562/544 |
| 3,284,492 | 11/1966 | Fremery | 562/543 |
| 3,979,450 | 9/1976 | Moskovich | 562/543 |
| 4,340,753 | 7/1982 | Cella | 562/528 |

FOREIGN PATENT DOCUMENTS

| | | |
|---|---|---|
| 0021118 | 1/1981 | European Pat. Off. . |
| 0201179B1 | 2/1991 | European Pat. Off. . |
| 1093358 | 11/1960 | Germany . |
| 1239400 | 7/1971 | United Kingdom ............ 562/543 |

OTHER PUBLICATIONS

Fremery, M. I., et al, *J. Org. Chem.* 28:2537–2541 (1963).
Franz, J. E., et al, *J. Org. Chem.* 30:1488–1491 (1964).
Framz. K/E/. et a;. *J. Org. Chem. 30:4328–4330 (1965).*
Welch. C. M., *Textile Research J.* 58:480–486 (1988).

*Primary Examiner*—Michael L. Shippen
*Attorney, Agent, or Firm*—Connolly & Hutz

[57] ABSTRACT

The invention relates to a process for the preparation of polycarboxylic acids and derivatives thereof, the polycarboxylic acids prepared containing at least three carboxyl groups, comprising the steps (A) introducing one or more organic compounds, which contain nonaromatic carbon-carbon (C—C) double bonds, into water, (B) ozonolysis of the organic compounds in water by passing in an ozone-containing carrier gas, (C) addition of an aqueous hydrogen peroxide solution, to oxidatively work up the ozonolysis products produced in step (B), which comprises, in step (A), introducing the organic compound(s) into water having a pH of 7 or less than 7 and, in step (C), adding hydrogen peroxide in water without adding an organic solvent.

20 Claims, No Drawings

PROCESS FOR THE PREPARATION OF POLYCARBOXYLIC ACIDS AND DERIVATIVES THEREOF

This application is a continuation of application Ser. No. 07/875,386 filed Apr. 29, 1992, now abandoned.

The invention relates to a process for the preparation of polycarboxylic acids and derivatives thereof, the polycarboxylic acids prepared containing at least three carboxyl groups.

The invention relates in particular to the ozonolysis of organic compounds which contain nonaromatic C—C double bonds and the oxidative work-up of the ozonides, formed in the oxidation of the these organic compounds, with hydrogen peroxide to give polycarboxylic acids.

Carboxylic acids and polycarboxylic acids are starting materials for a multiplicity of industrial uses, such as for example the preparation of polyesters. In addition to such uses, typical polycarboxylic acids, such as for example 1,2,3,4-butanetetracarboxylic acid and 1,2,3,4-cyclopentanetetracarboxylic acid, can be used as cellulose crosslinkers (Textile Research Journal 58 (8) 480 (1998)).

Numerous methods are known for the preparation of carboxylic acids and polycarboxylic acids by oxidative cleavage of nonaromatic C—C double bonds. When cycloolefins are used as starting materials for the oxidative cleavage of carbon-carbon double bonds, ω,ω'-dicarboxylic acids can be prepared under suitable reaction conditions. When norbornene derivatives having a carboxyl group in the bicyclic ring system, such as for example norbornenecarboxylic acid, are used tricarboxylic acids can be prepared under suitable reaction conditions. When Dieis-Alder adducts are used, such as for example tetrahydrophthalic anhydride, which can easily be prepared by reaction of 1,3-butadiene as the diene with dienophiles such as maleic anhydride, maleic acid or fumaric acid, tetracarboxylic acids, such as 1,2,3,4-butanetetracarboxylic acid can be prepared under suitable reaction conditions.

In addition to the cleavage of the C—C double bond by permanganate, tungstic acid or osmium tetroxide with suitable cooxidants, cleavage of the C—C double bond by ozone is a method which has long been known. In this case, the olefinic starting compound is treated in a solvent with an ozone-containing carrier gas, usually oxygen. If the reaction is carried out in an aprotic solvent, such as for example methylene chloride or esters (reaction I), secondary ozonides of type I are formed; in protic solvents, such as for example alcohols (R'—OH) or acids, peroxides of type II are formed, which can also occur as polymers, according to the following diagram:

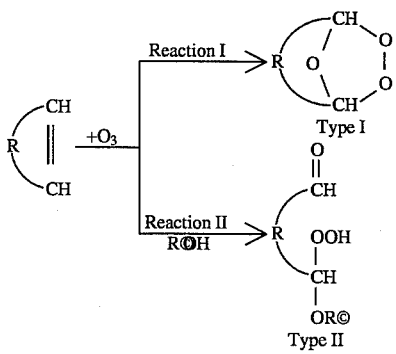

(R and R' are so-called organic radicals such as for example hydrocarbon radicals)

It is generally expedient to carry out the ozonolysis in protic solvents, since the ozonides of type I are frequently explosive compounds, which precipitate from the solvent on account of their low solubility (see "Ozonization in Organic Chemistry", P. S. Bailey, Academic Press, New York/London, 1978). If the ozonolysis products of type I or II are reacted with oxidants, the corresponding dicarboxylic acid compounds are obtained. The oxidants used can be peroxy carboxylic acids for example peroxyacetic acid, in situ peroxy acids for example formic acid with hydrogen peroxide or acetic acid with hydrogen peroxide in the presence of a catalytic amount of a strong Brönstedt acid such as sulfuric acid, and also alkaline hydrogen peroxide solution and oxygen.

As an example for the synthesis of polycarboxylic acids, the synthesis of 1,2,3,4-butanetetracarboxylic acid, subsequently termed BTCA, may be described on the basis of a number of publications and patents.

W. S. Knowles et al. describe the preparation of BTCA by a vanadium-catalyzed nitric acid oxidation in J. Org. Chem 30 (1965) 1488.

In EP-A 0 021 118, BTCA is prepared by a ruthenium-catalyzed coupled oxidation of tetrahydrophthalic anhydride and acetaldehyde. This has as a consequence the unavoidable production of many times the molar amount of acetic acid.

EP-A 0 201 719 discloses oxidation by means of tungstic acid and hydrogen peroxide. The high catalyst costs and the necessary excess of hydrogen peroxide are disadvantageous in this case. In all metal-catalyzed processes, the problem of removal of the catalyst arises. Depending on the use of the BTCA and toxicity of the metal, removal is necessary as far the limit of detection.

Synthesis of BTCA by ozonolysis of tetrahydrophthalic acid or its anhydride with subsequent oxidation of the resulting ozonides is also known.

U.S. Pat. No. 3,218,353 discloses a process for the preparation of 1,2,3,4-butanetetracarboxylic acid and 1,2,3,4-cyclopentanetetracarboxylic acid by ozonolysis of olefins and subsequent oxidative decomposition of the resulting ozonides in solvents such as methanol, ethyl acetate and glacial acetic acid.

In J. Org. Chem. 30 (1965) 4328, J. E. Franz, W. S. Knowles and C. Osuch describe a process for the preparation of meso-1,2,3,4-butanetetracarboxylic acid in acetic acid and formic acid, the subsequent oxidation of the resulting ozonides being carried out by a peroxycarboxylic acid, which is either added directly or is prepared in situ as described. The in situ method requires in any case the use of an acid as solvent. When the in situ method is used, a low water content, i.e. the use of an acid as free from water as possible, is reported as expedient, since the water content affects the acid/peracid equilibrium. When acetic acid is used, to adjust the equilibrium, a small amount of a stronger acid, for example sulfuric acid, is required, which under some circumstances can only be removed from the product with difficulty. The ecologically and economically necessary recovery of the acid used is associated with at least a marked technical effort. When formic acid is used, complete recovery is actually impossible, since this decomposes under thermal stress. If, instead of an acid, another solvent is used for the ozonolysis, such as for example methanol, a change of solvent is necessary for the oxidative work-up. This is a marked disadvantage, since energy is required for the separation by distillation. Furthermore, the concentration of the peroxidic reaction products involves an often not insubstantial safety risk.

In U.S. Pat. No. 3,284,492 and J. Org. Chem. 28 (1963) 2537, ozonolysis in aqueous emulsion is described. In this case, the aqueous phase must contain hydrogen peroxide and sodium hydroxide. The sodium salt of the corresponding acid is thereby obtained. In a second reaction step, this is converted into the free carboxylic acid by addition of hydrochloric acid, which has, as a consequence, the unwanted unavoidable production of sodium chloride. It is likewise a disadvantage, that the alkaline environment accelerates the speed of decomposition of the hydrogen peroxide.

The object was therefore to develop a process for the production of polycarboxylic acids and derivatives thereof, which avoids the abovementioned disadvantages.

This object is achieved by the process having the characteristics mentioned in claim 1. The dependent claims describe particular embodiments of this process.

In the process according to the invention, in step (A), the organic compound is first introduced into the reaction medium water, deionized water being normally used. The quality of the water used determines the purity of the prepared end product. The process according to the invention is distinguished in that the organic compound need not be completely dissolved in the reaction medium. The process according to the invention can be carried out with a solution, an emulsion and also with a suspension of the organic compound in water. The only precondition for carrying out the process according to the invention is partial solution of the introduced organic compound in the reaction medium, where the amount of the dissolved organic compound can even be in the range of the limit of detection. Water, in all the steps (A), (B) and (C) of the process according to the invention, is both reaction medium and solvent.

Carrying out the process according to the invention using a suspension of the starting compound to be reacted is surprising, since the known processes for the preparation of polycarboxylic acids provide for use of the compound in solution or in emulsion using an emulsifier.

In a further step (B) of the process according to the invention the ozonolysis of the organic compounds is carried out in the reaction medium water. In the process according to the invention, it has surprisingly been found that the ozonolysis of organic compounds can be carried out in water, regardless of the form in which these organic compounds are present in water, be it as solution, emulsion, or even as suspension in water.

In step (C) of the process according to the invention, an aqueous solution of hydrogen peroxide is added. This leads to an oxidative work-up of the ozonide present after the ozonolysis to give the polycarboxylic acid. It has surprisingly been found that the oxidative work-up of the ozonolysis product can be carried out in water without addition of an acid as solvent by simple addition of aqueous hydrogen peroxide solution. This is surprising since the solubility of the free acid in water is markedly lower than the solubility of the sodium salt of the acid and the oxidative work-up can even be carried out in a suspension. The oxidative work-up in a suspension surprisingly succeeds in very good yields, although, by the presence of a suspension, only a small part of the resulting ozonide is available for reaction. The work-up in water is all the more surprising, since the oxidative work-up with hydrogen peroxide according to the prior art only succeeds readily with addition of organic acids such as formic acid. Even with the use of acetic acid, the addition of a stronger proton acid such as sulfuric acid is necessary, in order to form the peracid required, according to the literature, for the oxidative work-up of the ozonolysis products. The process according to the invention offers the possibility of carrying out the oxidative work-up of the ozonolysis products to give polycarboxylic acids in aqueous suspension without addition of an organic acid or a mixture of acids.

The successful oxidative work-up of the ozonolysis products to give polycarboxylic acids was especially unexpected, since the reaction in water is associated with a low concentration of hydrogen peroxide. Nevertheless, the oxidative work-up of the ozonolysis products in aqueous solution proceeds in at least comparable, on occasion even improved, yield in comparison to the hitherto known preparation processes.

The process according to the invention can be applied in all steps (A), (B) and (C) to a great number of organic compounds. These organic compounds can be used as individual compounds or in the form of mixtures of a plurality of compounds in steps (A), (B) and (C), where the number of individual components of a mixture used does not have to be restricted. Organic compounds is taken to mean compounds which contain nonaromatic carbon-carbon double bonds (C—C double bonds). Such organic compounds, which contain ethylenic double bonds in the sense of nonaromatic C—C double bonds, are generally termed olefins and will be subsequently so termed for reasons of brevity. It should be noted, that the term olefins is not restricted to compounds which only contain hydrogen and water. In other words: each organic compound (olefin) containing nonaromatic C—C double bonds is suitable to be reacted by the process according to the invention to give polycarboxylic acids or derivatives thereof. Depending on the structure of the olefin, the polycarboxylic acids formed are at least tricarboxylic acids. The olefins used are generally aliphatic alkenes, or aliphatic cycloalkenes having one or more C—C double bonds. Such olefins can also include in their structures substituents having an aromatic group, a halogen-containing group or a nitro, carboxyl, polycarboxyl, alkoxy, aryloxy or cyano group. Starting materials which can also be used are esters and/or half esters having nonaromatic C—C double bonds. Condensed ring systems in which an aromatic ring system is coupled to a cycloalkene ring, such as for example 1,4-dihydro-1,4-naphthalenedicarboxylic acid, can likewise be used for the preparation of polycarboxylic acids by the process according to the invention.

Bicyclic ring systems, such as for example norbornenedicarboxylic acid, or polycyclic ring systems, such as for example tetracyclo[$1^{6,9}.1^{4,5}.0^{5,10}$]-2,3-dicarboxy-7-decene, can likewise be used as olefinic starting materials for the preparation of the polycarboxylic acids. The bicyclic or polycyclic ring systems can also contain the abovementioned groups and aromatic ring systems, without their use in the process according to the invention being restricted.

So-called Diels-Alder products, which were prepared by reaction of a diene of the formula

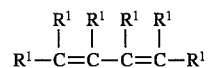

with a dienophile, selected from the group comprising unsaturated dicarboxylic acids of the formula

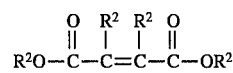

and anhydrides, esters and alkali metal salts of these dicarboxylic acids, where $R^1$ and $R^2$ are hydrogen, alkyl radicals or aryl radicals, are likewise suitable to be used as olefins for the preparation of polycarboxylic acids by the process according to the invention. Diels-Alder products which were prepared by reaction of a diene of the formula

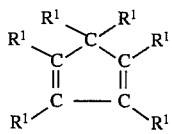

with one of the abovementioned dienophiles are likewise suitable for use in the process according to the invention.

To carry out the process according to the invention, in a step (A), the organic compound is first introduced into the reaction medium water. The reaction medium water into which the organic compound is introduced has a pH of 7 or less than 7. This introduction of the organic compound into the reaction medium can be carried out in various ways. The introduction can be carried out by placing the reaction medium water in the reaction vessel and adding the olefinic starting compound or a mixture of a plurality of starting compounds (discontinuous process) or by adding the reaction medium water and the olefinic starting compound or a mixture of a plurality of starting compounds simultaneously into the reaction vessel (continuous process). In this case, the reaction medium water and the starting compound or mixture of a plurality of starting compounds can be added to the reaction vessel in identical or different portions. Such a continuous process can be carried out for example in a bubble column. The ratio of water to the organic compound is only limited by the mixing necessary. The necessary mixing is achieved by a suitable stirring device (for example high speed stirrer), which assures a uniform distribution of the organic compound in the reaction medium. It can be advantageous to add the organic compound to the reaction medium already vigorously stirred. The mixture of reaction medium and organic compound, whether it be a solution, emulsion or suspension, is now heated for 15 to 30 minutes to temperatures of 30° C. to boiling temperature, preferably 80° C. to boiling temperature. The anhydride used thus gives the free carboxylic acid, which, in comparison to the corresponding anhydride, is soluble in water in a higher concentration, which is expedient for the reaction. However, this does not exclude also being able to carry out the reaction directly with the anhydride. If it is desired to prepare partially esterified carboxylic acids, the use of esters or half esters of the corresponding organic starting compound can also be expedient. The alcohol components used can be monohydroxy or polyhydroxy compounds having a backbone of 1 to 10 carbon atoms.

In step (B) of the process according to the invention, ozone is passed into the solution, emulsion or suspension, where, for better introduction of gas into the reaction batch, the stirring process should not be interrupted. Ozone can be used in an amount less than the stoichiometric amount to greatly above the stoichiometric amount. Preferably, 0.5 to 10, particularly preferably 1.0 to 1.2, equivalents of ozone are used per mole of nonaromatic double bond of the starting compound(s).

The ozone can be contained in a carrier gas for example oxygen or air, which itself has no disadvantageous effects on the reaction, or in an inert carrier gas such as, for example nitrogen. The concentration of ozone in the resulting ozone-containing carrier gas stream is not critical and extends over broad ranges. The ozone can preferably be contained in a carrier gas in a concentration of 0.1 to 30% by volume, particularly preferably 1 to 9% by volume. When the gas stream has a low content of ozone, this is passed into the stirred reaction mixture in a larger volume and for a longer period of time. If the concentration of ozone in the carrier gas is higher, smaller volumes of carrier gas are passed into the stirred reaction mixture. While the gas is being passed in, the reaction mixture, comprising the reaction medium water and the olefin used, should have a temperature between the solidification point of the solution and the boiling point of the solution, preferably a temperature of 0° to 30° C., particularly preferably a temperature of 5° to 15° C. We have found, surprisingly, that the ozonolysis actually gives the best reaction course at comparatively low temperature, although the solubility of the olefin used decreases with decreasing temperature. The inlet flow velocity of the ozone/carrier gas mixture is not critical. It is advantageously selected in dependence on the reaction temperature in such a manner that as complete as possible a conversion takes place and that no ozone, or only a small amount of ozone, escapes from the reaction vessel. This can mean that toward the end the inlet flow velocity and/or the ozone concentration is reduced.

In step (C) of the process according to the invention, the oxidative work-up of the reaction mixture is carried out. For this purpose, hydrogen peroxide solution is added to the reaction batch. Commercial hydrogen peroxide can be used. The hydrogen peroxide concentration of the solution added can be varied in broad ranges; preference is given to a concentration of 10 to 90% by weight, in particular a concentration of from 50 to 85% by weight of hydrogen peroxide. The amount of hydrogen peroxide used should be 0.1 to 10 equivalents, preferably 0.5 to 2 equivalents, particularly preferably 1.0 to 1.75 equivalents per mole of nonaromatic double bond of the starting compound(s) used. The hydrogen peroxide can also be added to the reaction solution prior to ozonolysis. It is also possible to add a catalytic amount of a strong acid, such as for example formic acid, with the hydrogen peroxide, which can be advantageous depending on the temperature of the work-up. However, it has surprisingly been shown that the oxidative work-up of the ozonolysis product can be carried out in the reaction medium water without addition of an acid as additional solvent and/or organic solvent. It is still more surprising that the oxidative work-up of the ozonolysis product can be carried out without addition of acid in at least comparable, on occasion even improved, yield. The reaction solution is now heated for 0.1 to 70 hours, preferably 3 to 30 hours, to a temperature of 20° C., preferably 40° C. to boiling temperature of the solution, in particular 60° to 80° C. Where required, any excess peroxide present may be decomposed by addition of a compound catalyzing the decomposition such as for example activated charcoal and/or heating to the boiling point of the solution. After a filtration, if required, the water is removed. This can take place by distillation under reduced pressure, for example in a rotary evaporator, or for example by spray-drying. In this case, it is again expedient that, by the use of water as reaction medium, the, under certain circumstances, laborious recovery of the solvent, which incurs additional safety measures, can be avoided.

The content of polycarboxylic acid in the residue obtained can be determined both by quantitative gas chromatography after silylation and by liquid chromatography (HPLC). The polycarboxylic acid obtained, depending on reaction conditions, in very good yields can be used for most applications without further purification operations. Any purification required can be carried out for example by recrystallization.

If half esters of polycarboxylic acids are prepared by the process according to the invention, their content in the residue obtained can likewise be determined by quantitative gas chromatography and by liquid chromatography (HPLC).

The quantitative determination of the polycarboxylate esters prepared is carried out by gas chromatography. In addition to the analytical methods already described for the determination of the content of end product, all methods which are used for the determination of the carboxyl content of an organic compound are suitable, such as for example acid-base titration or determination of the acid number.

The process described permits the preparation of polycarboxylic acids and derivatives thereof in very high yields. The process according to the invention is composed of a plurality of steps (A), (B) and (C), where it is possible, with respect to carrying out the process, that the addition of hydrogen peroxide (C) can be carried out before, during or after the ozonolysis of the starting compounds (B). The sequence of the individual reaction steps can be: (A) then (B) then (C) or (A) then (C) then (B) or (A) then (B) and (C).

The process according to the invention has marked economic and ecological advantages compared to the prior art, since at no point is the use of an organic solvent necessarily required. By carrying out the reaction in water, a laborious recovery and/or disposal of the solvent is dispensed with. The ozone and hydrogen peroxide oxidants used give oxygen and water as end products. No salt-type wastes result from the preparation. Metal catalysts are not used in the reaction. Contaminations by heavy metals are thus not possible, so that laborious purification and analysis is avoided.

The process according to the invention is illustrated in more detail by the following examples and comparison examples, which should not be taken to mean that the process according to the invention is restricted solely to these examples.

In the illustrative implementation of the process according to the invention, which is given by the subsequently listed examples, the reaction vessel was composed of a 2 l glass multi-necked flask, provided with a high speed stirrer, a gas feed tube with a gas frit, gas flushing and thermometer.

EXAMPLE 1

76.08 g (0.5 mol) of tetrahydrophthalic anhydride in 600 ml of water are refluxed for 1 hour in a 2 flask. After the mixture has cooled, oxygen having an ozone content of 2.9% by volume is passed into the vigorously stirred suspension at a flow rate of 100 l h$^{-1}$ through a frit for a period of 3 hours and 30 minutes. During this, the temperature between the solution is maintained at 20° to 25° C. 10 minutes prior to the end of the reaction, the gas introduction is briefly interrupted, in order to rinse down any solid suspended on the wall of the vessel. At the end of the reaction, 714 ml of a clear solution having a density of 1.056 g ml$^{-1}$ are obtained. The solution is divided into two.

a: 375 ml of the reaction solution are heated with 20 ml of 60 percent by weight hydrogen peroxide (437 mmol) for 15 hours at 70° to 80° C. The mixture is then refluxed and 500 mg of powdered activated charcoal are added. When the test for oxidant using KI/starch paper gives a negative result, the activated charcoal is filtered off. The solution obtained is concentrated to dryness in an oil pump vacuum. The residue is dried to constant weight at 60° C. 56.05 g of a finely crystalline powder are obtained, this corresponds to 95.7% of theory. The substance has a melting point of 181° to 186° C. The water content by Karl Fischer is 4.2% by weight, the content of butanetetracarboxylic acid (BTCA) is 93.4% by weight. This results in a yield of 89.4% of BTCA.

b: 0.1 ml of formic acid is added to the remaining 375 ml of reaction solution. The procedure as described under a: is then carried out. 55.36 g of a solid are obtained, which corresponds to 94.6% of theory. This has a content of 88.9% by weight of BTCA, giving a yield of 84.1% of BTCA.

EXAMPLE 2

The initial batch corresponds to Example 1, but 106.52 g (0.7 mol) of tetrahydrophthalic anhydride are used. Gas is passed in for 6 hours and 30 minutes. 670 ml of reaction solution are obtained having a density of 1.084 g cm$^{-3}$. The batch is divided into two.

19 ml of 60 percent by weight hydrogen peroxide (416 mmol) are added to 335 ml of reaction solution and the mixture is heated for 24 hours at 70° C., 1 g of powdered activated charcoal is added and the mixture is refluxed for 4 hours. 78 g of a solid are obtained, corresponding to 95.2% of theory. The substance has a melting point of 183° to 186° C. A content of 95.2% by weight of BTCA results from quantitative GC and HPLC, from which a yield of 90% is deduced.

The second half is treated analogously, but after the hydrogen peroxide addition, the mixture is refluxed for 4 hours. A weight of 75.13 g of a white powder is obtained, 91.7% of theory. The substance has a melting point of 183° to 186° C. From a content of 88.9% by weight of BTCA, a yield of 81.5% results.

EXAMPLE 3

The initial batch corresponds to Example 2, but this is not divided and the hydrogen peroxide (38 ml; 60% by weight; 832 mmol) is added prior to ozonolysis. Following ozonolysis, the mixture is heated for 14 h at 70° C. Weight: 153.54 g of a white powder equal to 93.7% of theory. The substance has a melting point of 183° to 184° C.

EXAMPLE 4

164.16 g (1 mol) of norbornene-2,3-dicarboxylic anhydride are refluxed in 500 ml of water for 1 hour. On cooling to room temperature, the majority of the free acid precipitates. 1.1 mol of ozone are passed into the suspension obtained at an internal temperature of 0° to 10° C. in the course of 4 hours. The flow rate is varied during this between 100 and 200 l h$^{-1}$. 32.5 ml of 85 percent by weight hydrogen peroxide (1.1 mol) are then added and the mixture is first heated for 12 hours at 75° C., then for 3 hours at boiling point. After addition of 1 g of powdered activated charcoal, the mixture is further heated until the test for oxidant using KI/starch paper is negative. After filtration of the activated charcoal, the solvent is removed on a rotary evaporator and the residue obtained is dried to constant weight. 241 g of a white solid are obtained, corresponding to 98% of theory.

This was identified by 1H-NMR spectroscopy and also gas chromatography using mass-selective detection as cyclopentanetetracarboxylic acid.

EXAMPLE 5

110 mmol of ozone are passed into an emulsion of 12 ml (99.6 mmol) of (2-cyclopenten-1-yl)acetic acid and 30 ml of water at 0° to 5° C. in the course of 30 minutes. Subsequently, 3.75 ml of 85 percent by weight hydrogen peroxide (125 mmol) are added and the temperature is elevated for 12 h to 70° C. The mixture is then refluxed and 250 mg of powdered activated charcoal are added. When a test for oxidants using KI/starch paper is negative, the activated charcoal is filtered off and the solvent is removed. The residue is dried to constant weight.

A weight of 15.4 g of yellowish powder is obtained, which corresponds to 81% of theory. This is identified by 1H-NMR spectroscopy and gas chromatography using mass-selective detection as 1,2,4-butanetricarboxylic acid.

We claim:

1. A process for the preparation of a polycarboxylic acid having at least three carboxyl groups, consisting of the steps
   (A) introducing one or more aliphatic cycloalkenes into water, wherein said aliphatic cycloalkenes have one or more carbon-carbon double bonds, and further wherein said aliphatic cycloalkenes include in their structures substituents having an aromatic group, a halogen-containing group, a nitro group, a carboxyl group, a polycarboxyl group, an alkoxy group, an aryloxy group or a cyano group,
   (B) ozonolysis of said aliphatic cycloalkene(s) in water by passing in an ozone-containing carrier gas, and
   (C) addition of an aqueous hydrogen peroxide solution, to oxidatively work up the ozonolysis products produced in step (B), which comprises, in step (A), introducing the aliphatic cycloalkene(s) into water having a pH of 7 or less than 7 and, in step (C), adding hydrogen peroxide in water without adding an organic solvent or an acid.

2. The process as claimed in claim 1, wherein the aliphatic cycloalkene(s) is (are) used in aqueous solution, emulsion suspension.

3. The process as claimed in claim 1, wherein the aliphatic cycloalkene(s) used is (are) tetrahydrophthalic acid and/or norbornenedicarboxylic acid.

4. The process as claimed in claim 1, wherein, in step (B), 0.5 to 10, equivalents of ozone are used per mole of nonaromatic double bond of the aliphatic cycloalkene(s).

5. The process as claimed in claim 1, wherein the ozone is contained in a carrier gas at a concentration of 0.1 to 30% by weight.

6. The process as claimed in claim 1, wherein the ozonolysis is carried out at a temperature of at most the boiling point of the solution.

7. The process as claimed in claim 1, wherein the amount of hydrogen peroxide used is 0.1 to 10 equivalents, per mole of nonaromatic double bond of the aliphatic cycloalkene(s).

8. The process as claimed in claim 1, wherein the sequence of the reaction steps is (A) then (B) then (C) or (A) then (C) then (B) or (A) then (B) and (C).

9. The process as claimed in claim 1, wherein hydrogen peroxide is added during the ozonolysis.

10. The process as claimed in claim 1, wherein the reaction solution is heated for the oxidative work-up of the ozonolysis products to a temperature of from at least 20° C., to the boiling temperature of the solution.

11. The process as claimed in claim 1, wherein, in step B, said aliphatic cycloalkene(s) is/are treated with 1.0 to 1.2 equivalents of ozone per mole of nonaromatic carbon-carbon double bond of said aliphatic cycloalkene(s).

12. The process as claimed in claim 1, wherein the ozone of said step B is contained in the carrier gas at a concentration of 1 to 9% by weight.

13. The process as claimed in claim 1, wherein said step B is carried out at a temperature within the range of 0° to 30° C.

14. The process as claimed in claim 13, wherein said temperature is within the range of 5° to 15° C.

15. The process as claimed in claim 1, wherein the amount of hydrogen peroxide added to oxidatively work up said ozonolysis product is 0.5 to 2 equivalents per mole of nonaromatic carbon-carbon double bond of said aliphatic cycloalkene(s).

16. The process as claimed in claim 15, wherein said amount of hydrogen peroxide is 1.0 to 1.75 equivalents per mole of said nonaromatic carbon-carbon double bond.

17. The process as claimed in claim 1, wherein the aqueous reaction medium is heated to a temperature of about 60° to 80° C. for the oxidative work-up of said ozonolysis product.

18. The process as claimed in claim 1, wherein the aliphatic cycloalkene used is 1,4-dihydro-1,4-naphthalene-dicarboxylic acid.

19. The process as claimed in claim 1, wherein the aliphatic cycloalkene used is tetracyclo($1^{6,9}.1^{1,4}.0^{5,10}$)-2,3-dicarboxy-7-decene.

20. The process as claimed in claim 1, wherein the aliphatic cycloalkene used is (2-cyclopenten-1-yl)acetic acid.

* * * * *